United States Patent
Alobaid

(10) Patent No.: US 8,734,459 B1
(45) Date of Patent: May 27, 2014

(54) DEVICE AND METHOD TO PREVENT EXTRAVASATION OF BONE CEMENT USED IN BALLOON KYPHOPLASTY

(71) Applicant: Abdulrazzaq Alobaid, Safat (KW)

(72) Inventor: Abdulrazzaq Alobaid, Safat (KW)

( * ) Notice: Subject to any disclaimer, the term of this patent is extended or adjusted under 35 U.S.C. 154(b) by 0 days.

(21) Appl. No.: 13/854,886

(22) Filed: Apr. 1, 2013

Related U.S. Application Data

(60) Provisional application No. 61/753,687, filed on Jan. 17, 2013.

(51) Int. Cl.
*A61B 17/58* (2006.01)
*A61B 17/60* (2006.01)
*A61B 17/00* (2006.01)

(52) U.S. Cl.
USPC .......................................... 606/92; 623/17.12

(58) Field of Classification Search
USPC .............................. 606/93, 94, 105; 623/17.12
See application file for complete search history.

(56) References Cited

U.S. PATENT DOCUMENTS

| | | |
|---|---|---|
| 6,361,539 B1 | 3/2002 | Heller et al. |
| 7,563,284 B2 * | 7/2009 | Coppes et al. ............. 623/17.12 |
| 2004/0073308 A1 * | 4/2004 | Kuslich et al. ............. 623/17.11 |
| 2006/0182780 A1 | 8/2006 | Riley et al. |
| 2006/0217736 A1 | 9/2006 | Kaneko et al. |
| 2010/0241178 A1 | 9/2010 | Tilson et al. |
| 2012/0004728 A1 | 1/2012 | Kohm et al. |
| 2012/0032374 A1 | 2/2012 | Bratt et al. |

FOREIGN PATENT DOCUMENTS

| | | |
|---|---|---|
| DE | 102009011561 A1 | 9/2010 |
| WO | WO 2006112941 A2 | 10/2006 |
| WO | WO 2009053820 A1 | 4/2009 |

\* cited by examiner

*Primary Examiner* — Andrew Yang
(74) *Attorney, Agent, or Firm* — Richard C. Litman

(57) ABSTRACT

The method for preventing extravasation of bone cement used in balloon kyphoplasty involves first forming a void in a vertebral body. A pair of unfilled balloons are then inserted into the void in the vertebral body. An injection tube or catheter is inserted through an inlet port of each of the balloons, and the balloons are filled with bone cement. The injection tubes are then removed from the inlet ports. The bone cement is preferably provided in the form of pellets or granules. The inlet ports are each provided with a seal, such as an elastic band mounted thereabout, or the like, allowing the inlet port to be automatically sealed as soon as the corresponding injection tube is withdrawn. The device includes at least the balloon and the seal, but may be furnished as a kit that also includes the bone cement and injection tube.

7 Claims, 6 Drawing Sheets

DEVICE AND METHOD TO PREVENT EXTRAVASATION OF BONE CEMENT USED IN BALLOON KYPHOPLASTY

CROSS-REFERENCE TO RELATED APPLICATION

This application claims the benefit of U.S. Provisional Patent Application Ser. No. 61/753,687, filed Jan. 17, 2013.

BACKGROUND OF THE INVENTION

1. Field of the Invention

The present invention relates to spinal surgery, and particularly to a device and method to prevent extravasation of bone cement used in balloon kyphoplasty.

2. Description of the Related Art

Kyphoplasty is a spinal procedure, in which bone cement is injected through a small hole in the skin, percutaneously, into a fractured vertebra with the goal of relieving the back pain of vertebral compression fractures. Kyphoplasty is a variation of a vertebroplasty. Kyphoplasty attempts to restore the height and angle of kyphosis of a fractured vertebra (of certain types), followed by its stabilization using injected bone cement. The procedure typically includes the use of a small balloon that is inflated in the vertebral body to create a void within the cancellous bone prior to cement delivery. Once the void is created, bone cement is injected with a biopsy needle into the collapsed or fractured vertebra. The needle is placed with fluoroscopic x-ray guidance. The cement (most commonly PMMA, although more modern cements are used as well) quickly hardens and forms a support structure within the vertebra that provides stabilization and strength. The needle makes a small puncture in the patient's skin that is easily covered with a small bandage after the procedure. In kyphoplasty, the bone cement is typically delivered directly into void which was created by the inflation of the balloon.

However, due to compression damage and/or other fractures in the vertebra, following injection of the cement, the injected bone cement often leaks through the cracks and fractures in the vertebra, a process called extravasation. The setting of this leaked cement can cause nerve damage, including nerve compression, along with other conditions, such neuropathy, lung embolus or the like.

Thus, a device and method to prevent extravasation of bone cement used in balloon kyphoplasty solving the aforementioned problems is desired.

SUMMARY OF THE INVENTION

The device and method to prevent extravasation of bone cement used in balloon kyphoplasty prevent the harmful leakage, or extravasation, of bone cement in kyphoplasty procedures. As is well known in kyphoplasty procedures, a void is first formed in a vertebral body. A pair of unfilled balloons are then inserted into the void in the vertebral body. The balloons are formed from any suitable bio-absorbable material, such as a bio-absorbable fibrous mesh or the like. An injection tube or catheter is respectively inserted through an inlet port of each of the balloons, and each balloon is filled with bone cement.

Any suitable type of bone cement may be utilized to fill the balloon. As an alternative to conventional liquid bone cement, a pelletized or granular bone cement may be injected. Further, pellets or capsules of air or silica, or combinations thereof, may alternatively be injected, or may be injected in combination with the pelletized or granulated cement. Such pellets, capsules and granules each have a size and shape allowing for injection via the conventional injection catheter or tube without the clogging thereof.

Once each balloon has been filled with the bone cement, the corresponding injection tube is removed from the respective inlet port. Each inlet port is provided with a seal, such as an elastic band mounted thereabout, or the like, allowing the inlet port to be automatically sealed as soon as the injection tube is withdrawn. It should be understood that any suitable type of band, seal, clamp, lock, collar or other sealing member may be utilized for sealing the inlet port. As an alternative, only a single balloon and a single corresponding injection tube may be utilized.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
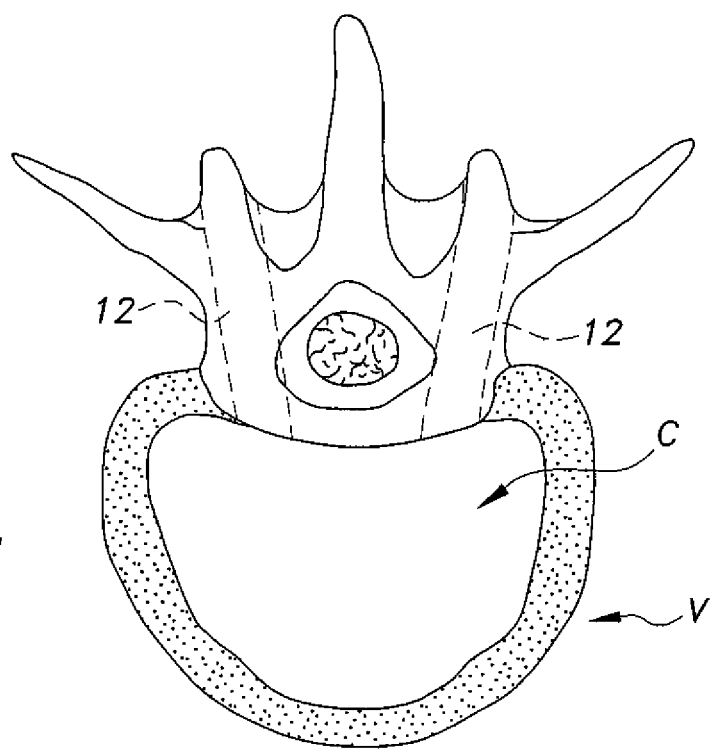
FIG. 1 illustrates a vertebral body following a kyphoplasty procedure to form a void therein.
Figure 2:
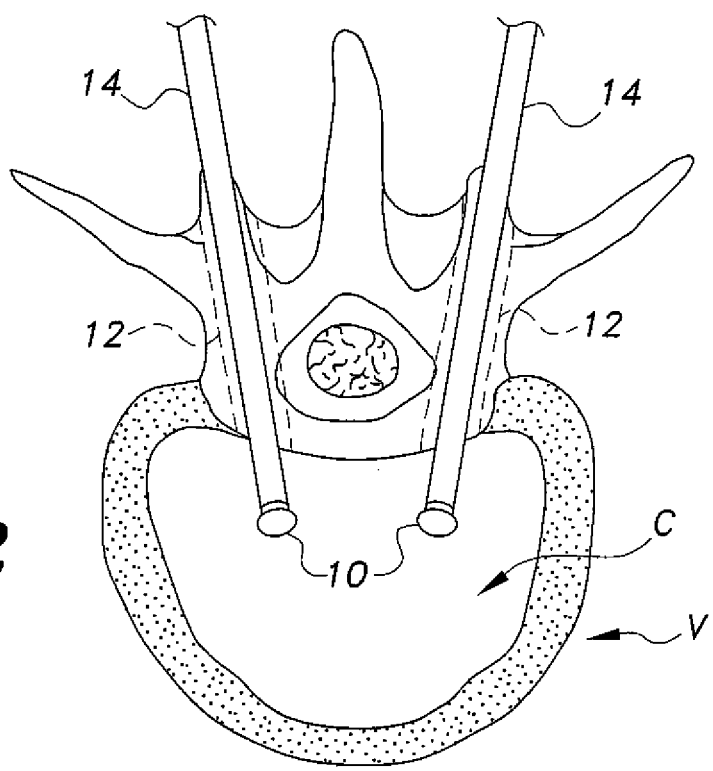
FIG. 2 illustrates placement of a pair of devices to prevent extravasation of bone cement used in balloon kyphoplasty according to the present invention.
Figure 3:
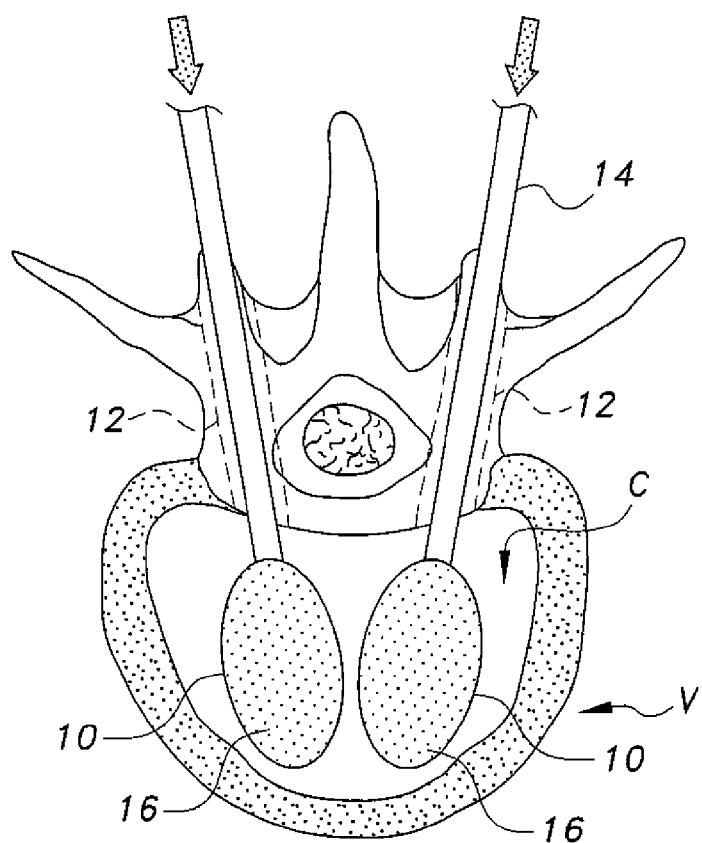
FIG. 3 illustrates filling of the devices to prevent extravasation of bone cement used in balloon kyphoplasty with bone cement.

FIG. 1 shows a vertebral body V in which a void or cavity C has been created by a conventional kyphoplasty procedure, as described above. As is typical in kyphoplasty, a pair of bore holes 12 have been formed in the vertebral body V. As shown in FIG. 2, an injection tube 14 is inserted through each one of the bore holes 12. The tip of each injection tube 14 carries a device 10 to prevent extravasation of bone cement. As shown in FIG. 3, each device 10 is in the form of a balloon or other type of fillable membrane. Each one of the pair of devices 10 is filled with bone cement 16 through injection tube 14. It should be understood that each device 10 may be formed from any suitable bio-absorbable material, such as a bio-absorbable fibrous mesh or the like. Similarly, each device 10 may be filled with bone cement 16 by any suitable method. Examples of such filling with bone cement or the like during kyphoplasty procedures are shown in U.S. Patent Application Publication No. US 2006/0217736 A1, to Kaneko et al., and U.S. Patent Application Publication No. US 2006/0182780 A1, to Riley et al., each of which is hereby incorporated by reference in its entirety.

It should further be understood that any suitable type of bone cement may be utilized. As an alternative to conventional liquid bone cement, a pelletized or granular bone cement may be injected. One example of such a granulated bone cement is SerenoCem™, manufactured by Corinthian Medical Limited Corporation of the United Kingdom. Another such pelletized bone cement is shown in U.S. Patent Application Publication No. US 2012/0032374 A1, to Bratt et al., which is hereby incorporated by reference in its entirety. Further, it should be understood that pellets or capsules of air or silica, or combinations thereof, may alternatively be injected, or may be injected in combination with the pelletized or granulated cement. Such pellets, capsules and granules each have a size and shape allowing for injection via conventional injection catheter or tube 14 without the clogging thereof.

Figure 4:
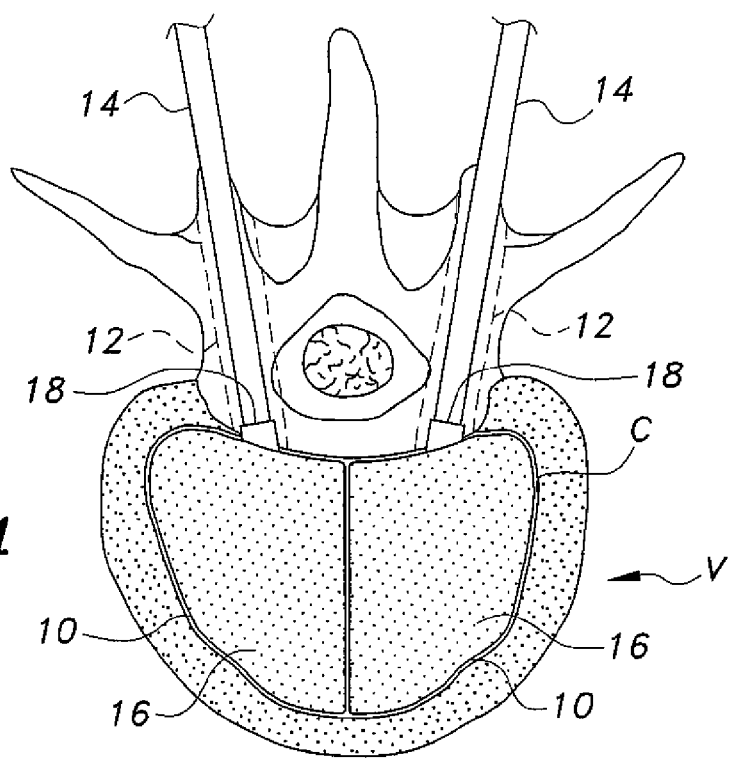
FIG. 4 illustrates the device to prevent extravasation of bone cement used in balloon kyphoplasty filled with the bone cement.
Figure 5:
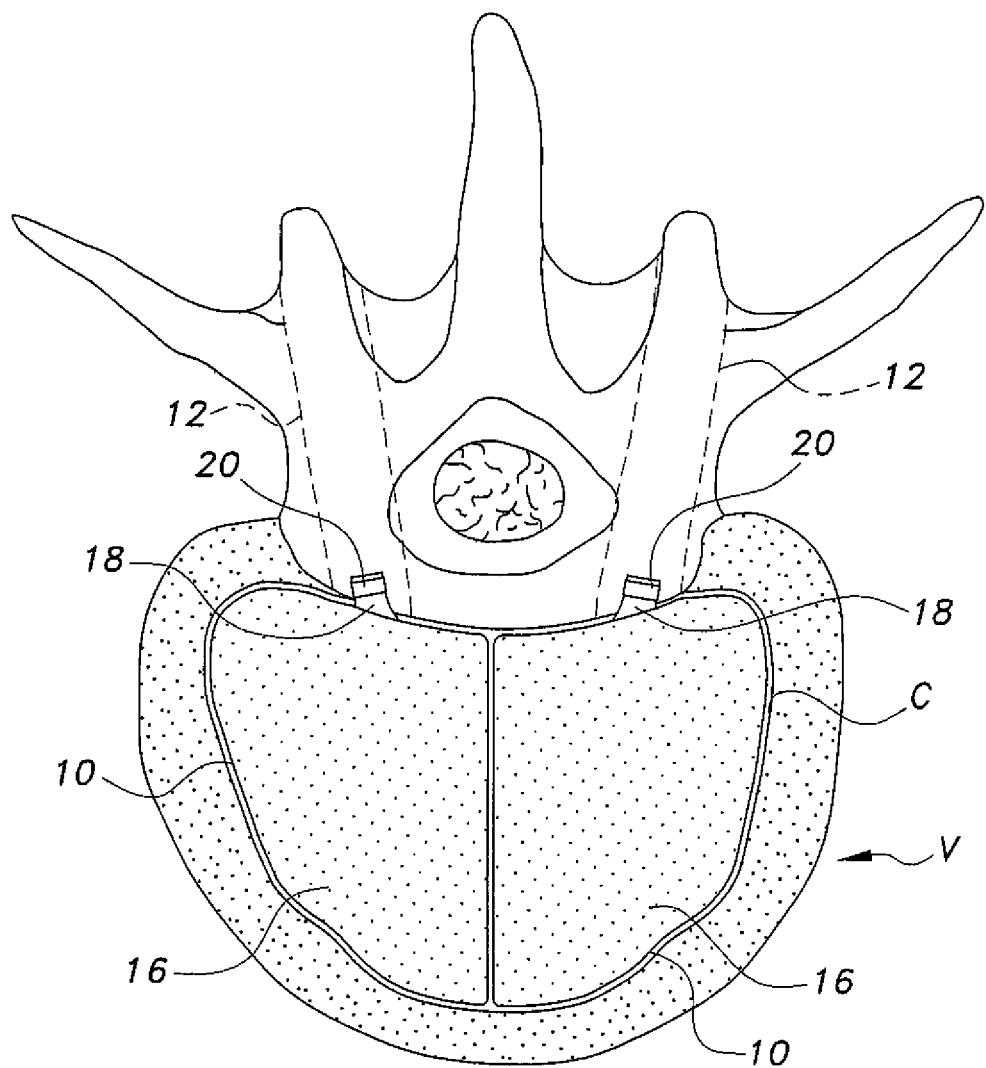
FIG. 5 illustrates removal of an injection tube and self-sealing of the device to prevent extravasation of bone cement used in balloon kyphoplasty.

As best seen in FIG. 4, the tip of each injection tube 14 is preferably inserted through a port 18 of the corresponding device 10. Once each device 10 is filled with cement 16, as shown in FIG. 4, the injection tube 14 is removed from port 18. The pair of devices 10 fill the cavity C, as shown in FIG. 4. As shown in FIG. 5, each port 18 is preferably surrounded by an elastic band seal 20, such as that commonly used in gall bladder procedures and the like, which elastically compresses the port 18 shut, thus preventing leakage of cement 16 from within the interior of the device 10. It should be understood that any suitable type of band, seal, clamp, lock, collar or other sealing member may be utilized for sealing port 18.

Once full, and once port 18 is sealed, the cement 16 dries and hardens. The pair of devices 10 prevent leakage of the cement during the hardening process. As noted above, each device 10 is in the form of a balloon or the like, formed from a bio-absorbable material. Thus, the balloon simply degrades following hardening of the cement 16.

Figure 6:
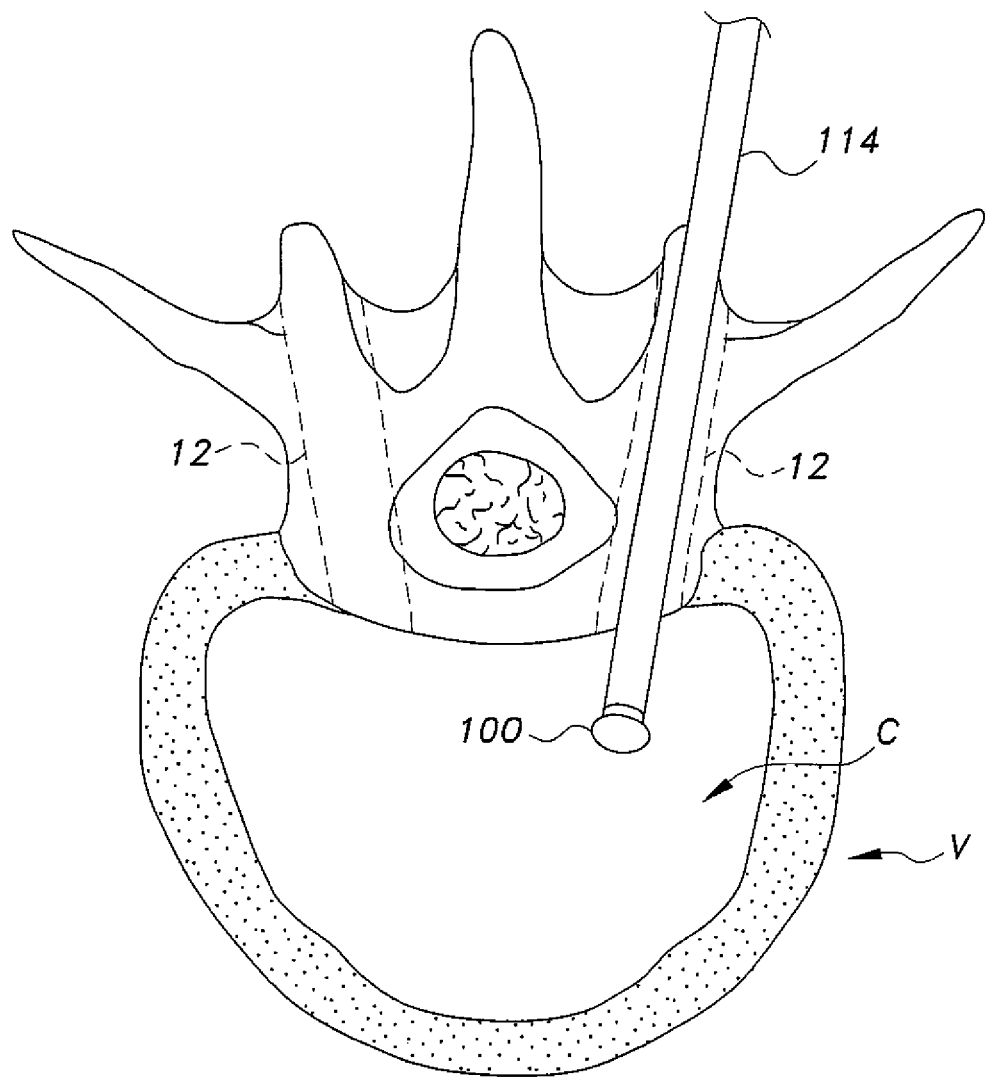
FIG. 6 illustrates placement of an alternative embodiment of the device to prevent extravasation of bone cement used in balloon kyphoplasty according to the present invention.
Figure 7:
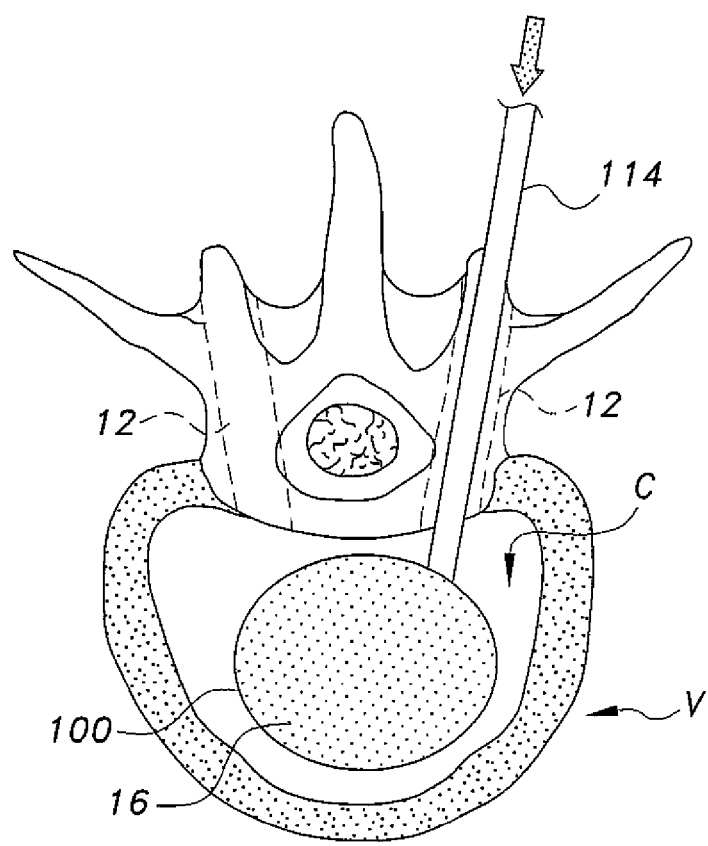
FIG. 7 illustrates filling of the device to prevent extravasation of bone cement used in balloon kyphoplasty of FIG. 6 with bone cement.

In the alternative embodiment of FIGS. 6-9, only a single balloon device 100 is utilized. As shown in FIG. 6, an injection tube 114 is inserted through only one of the bore holes 12. The tip of the injection tube 114 carries device 100 to prevent extravasation of bone cement. As shown in FIG. 7, the single device 100 is in the form of a balloon or other type of fillable membrane. As in the previous embodiment, device 100 is filled with bone cement 16 through the single injection tube 114. It should be understood that device 100 may be formed from any suitable bio-absorbable material, such as a bio-absorbable fibrous mesh or the like. Similarly, device 100 may be filled with bone cement 16 by any suitable method.

Figure 8:
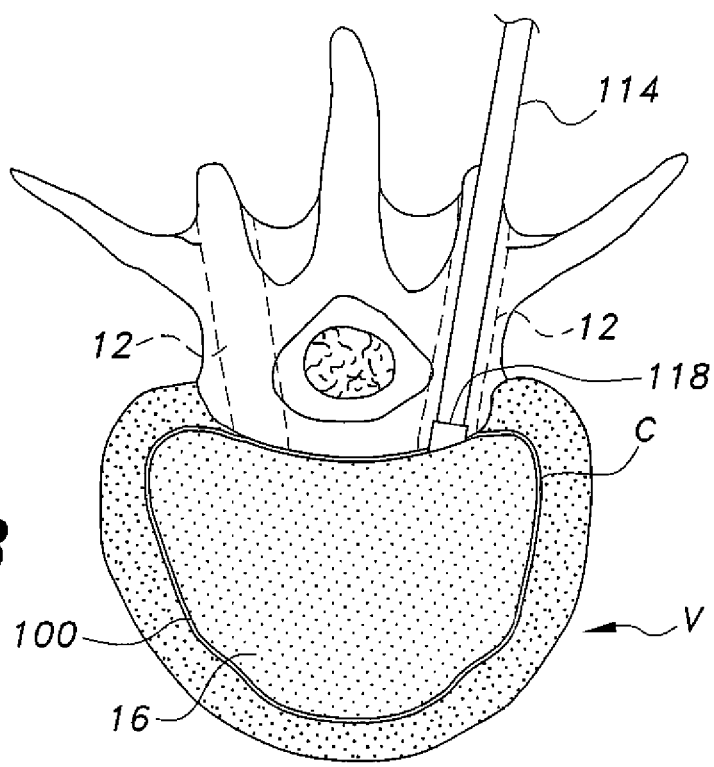
FIG. 8 illustrates the device to prevent extravasation of bone cement used in balloon kyphoplasty of FIG. 6 filled with the bone cement.
Figure 9:
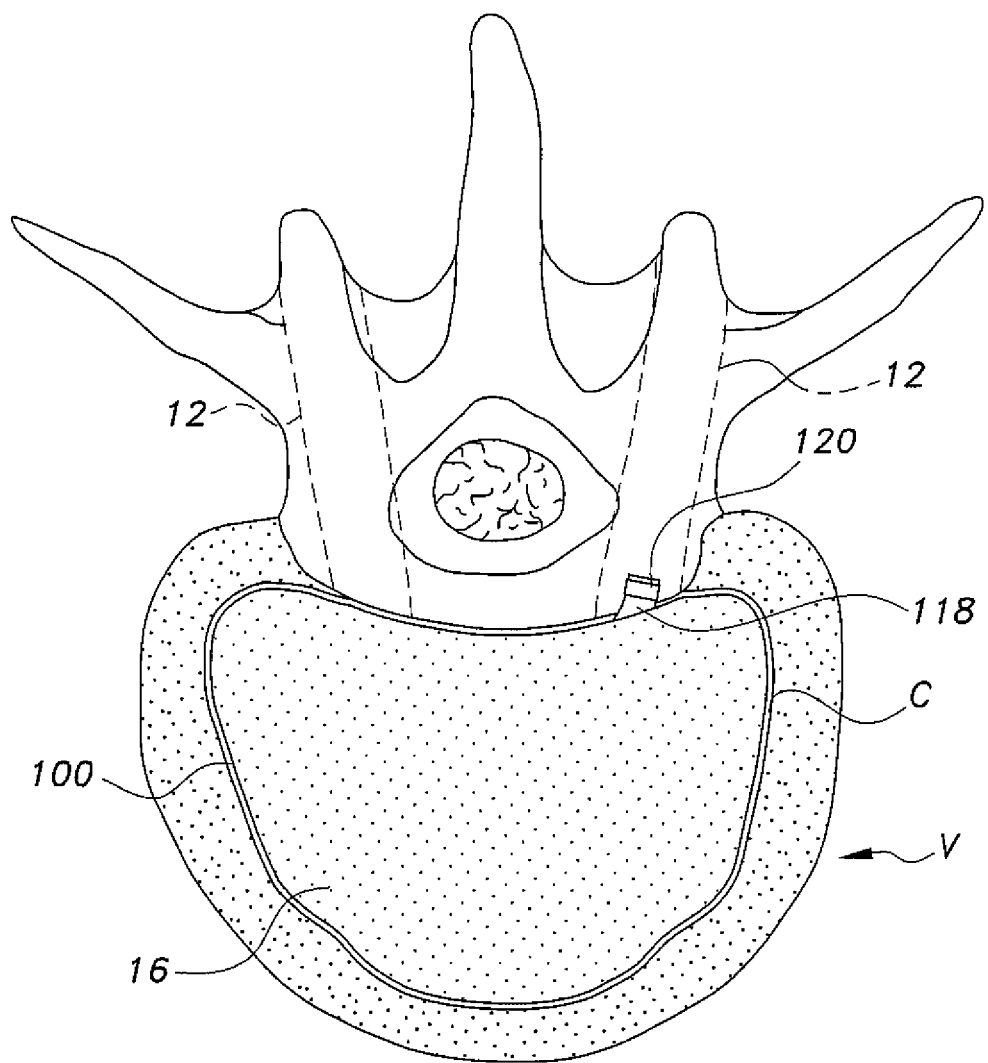
FIG. 9 illustrates removal of an injection tube and self-sealing of the device to prevent extravasation of bone cement used in balloon kyphoplasty of FIG. 6.

As best seen in FIG. 8, the tip of the single injection tube 114 is preferably inserted through a port 118 of the device 10. As in the previous embodiment, once the device 100 is filled with cement 16, as shown in FIG. 8, the injection tube 114 is removed from port 118. As shown in FIG. 9, each port 118 is preferably surrounded by an elastic band seal 120, such as that commonly used in gall bladder procedures and the like, which elastically compresses the port 118 shut, thus preventing leakage of cement 16 from within the interior of the device 100. It should be understood that any suitable type of band, seal, clamp, lock, collar or other sealing member may be utilized for sealing port 118.

It is to be understood that the present invention is not limited to the embodiments described above, but encompasses any and all embodiments within the scope of the following claims.

I claim:

1. A device to prevent extravasation of bone cement used in balloon kyphoplasty, consisting of:
    at least one balloon formed from bio-absorbable material, the at least one balloon having an inlet port;
    bone cement comprising a plurality of bone cement pellets; and
    a seal for sealing the inlet port, the seal including an elastic band mounted about the inlet port;
    wherein the at least one balloon is adapted for insertion into a void created in a vertebral body during kyphoplasty, the at least one balloon being filled with bone cement by at least one injection tube inserted through the inlet port, the seal sealing the inlet port once the balloon has been filled with the bone cement and the at least one injection tube has been removed therefrom.

2. A kit for preventing extravasation of bone cement used in balloon kyphoplasty, comprising:
    at least one balloon formed from bio-absorbable material, the at least one balloon having an inlet port;
    bone cement; and
    a seal for sealing the inlet port, the seal including an elastic band mounted about the inlet port;
    wherein the bone cement comprising a plurality of bone cement pellets; and
    at least one injection tube;
    wherein the at least one balloon is adapted for insertion into a void created in a vertebral body during kyphoplasty, the at least one balloon being filled with bone cement by at least one injection tube inserted through the inlet port, the seal sealing the inlet port once the balloon has been filled with the bone cement and the at least one injection tube has been removed therefrom.

3. The device to prevent extravasation of bone cement used in balloon kyphoplasty as recited in claim 2, wherein said at least one balloon comprises a pair of balloons.

4. A method of preventing extravasation of bone cement used in balloon kyphoplasty, comprising the steps of:
    providing a kit according to claim 2;
    forming a void in a vertebral body during kyphoplasty;
    inserting the at least one balloon into the void in the vertebral body, the at least one balloon having an inlet port;
    simultaneously filling each of the at least one balloon with bone cement through an injection tube inserted through the inlet port;
    removing the injection tube from the inlet port once each of the at least one balloon is filled with the bone cement; and
    sealing the inlet port following removal of the injection tube.

5. The method of preventing extravasation of bone cement used in balloon kyphoplasty as recited in claim 4, wherein the step of filling each of the at least one balloon with the bone cement comprises filling the balloon with a pelletized bone cement.

6. The method of preventing extravasation of bone cement used in balloon kyphoplasty as recited in claim 5, wherein the step of sealing the inlet port comprises elastically sealing the inlet port.

7. A method of preventing extravasation of bone cement used in balloon kyphoplasty, consisting of the steps of:
    forming a void in a vertebral body during kyphoplasty;
    inserting a pair of unfilled balloons into the void in the vertebral body, each of the balloons having an inlet port;
    simultaneously filling each of the balloons with bone cement through a pair of injection tubes respectively inserted through the inlet ports of each of the balloons;

removing the injection tubes from the inlet ports once the balloons are filled with the bone cement; and sealing each of the inlet ports following removal of the injection tube;

wherein the step of filling the balloons with the bone cement comprises filling the balloons with a pelletized bone cement; and wherein the step of sealing each of the inlet ports comprises elastically sealing each of the inlet ports.

\* \* \* \* \*